(12) United States Patent
Burkholz et al.

(10) Patent No.: US 10,639,455 B2
(45) Date of Patent: May 5, 2020

(54) CLOSED IV ACCESS DEVICE WITH PADDLE GRIP NEEDLE HUB AND FLASH CHAMBER

(71) Applicant: Becton, Dickinson and Company, Franklin Lakes, NJ (US)

(72) Inventors: Jonathan Karl Burkholz, Salt Lake City, UT (US); Bart D. Peterson, Farmington, UT (US); Bin Wang, Sandy, UT (US); Ralph L. Sonderegger, Farmington, UT (US); Tyler Warner, Bluffdale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 271 days.

(21) Appl. No.: 15/286,188

(22) Filed: Oct. 5, 2016

(65) Prior Publication Data

US 2017/0120017 A1    May 4, 2017

Related U.S. Application Data

(60) Provisional application No. 62/247,617, filed on Oct. 28, 2015, provisional application No. 62/247,596, filed on Oct. 28, 2015, provisional application No. 62/296,383, filed on Feb. 17, 2016, provisional application No. 62/247,599, filed on Oct. 28, 2015, provisional application No. 62/247,607, filed on Oct. 28, 2015, provisional application No. 62/247,621, (Continued)

(51) Int. Cl.
*A61M 25/06* (2006.01)

(52) U.S. Cl.
CPC .... *A61M 25/0693* (2013.01); *A61M 25/0606* (2013.01); *A61M 25/0637* (2013.01)

(58) Field of Classification Search
CPC .......... A61M 25/0693; A61M 25/0606; A61M 25/0637
USPC ...................................................... 604/168.01
See application file for complete search history.

(56) References Cited

U.S. PATENT DOCUMENTS 3,046,984 A    7/1962 Eby
3,547,119 A    12/1970 Hall et al.
(Continued)

FOREIGN PATENT DOCUMENTS

CA    2 133 053 A1    3/1995
CN    101879341 A    11/2010
(Continued)

OTHER PUBLICATIONS

Silva, Elson, Email Regarding "Respecting Hydrology Science and IP Rights—US Pat. Application 20110130728," pp. 1-6 (Jun. 2, 2011).

*Primary Examiner* — Phillip A Gray
(74) *Attorney, Agent, or Firm* — Kirton & McConkie; Craig Metcalf; Kevin Stinger

(57) ABSTRACT

An IV access device can include a needle hub that incorporates a flash chamber. The flash chamber can be used to provide visual confirmation of proper catheter placement within a vein. The flash chamber can include a path-defining structure to facilitate identifying whether blood is continually flowing into the flash chamber. The flash chamber may also be removable from the needle hub. In some cases, the needle hub may include a paddle grip that facilitates insertion of the catheter and separation of the needle hub from the catheter adapter.

15 Claims, 13 Drawing Sheets

Related U.S. Application Data filed on Oct. 28, 2015, provisional application No. 62/247,624, filed on Oct. 28, 2015, provisional application No. 62/247,626, filed on Oct. 28, 2015, provisional application No. 62/296,385, filed on Feb. 17, 2016.

(56) References Cited

U.S. PATENT DOCUMENTS

| | | |
|---|---|---|
| 3,589,361 A | 6/1971 | Loper et al. |
| 3,827,434 A | 8/1974 | Thompson et al. |
| 3,853,127 A | 12/1974 | Spademan |
| 3,859,998 A | 1/1975 | Thomas et al. |
| 4,003,403 A | 1/1977 | Nehring |
| 4,043,346 A | 8/1977 | Mobley et al. |
| 4,099,528 A | 7/1978 | Sorenson et al. |
| 4,149,539 A | 4/1979 | Cianci |
| 4,172,448 A | 10/1979 | Brush |
| 4,177,809 A | 12/1979 | Moorehead |
| 4,193,399 A | 3/1980 | Robinson |
| 4,200,096 A | 4/1980 | Charvin |
| 4,269,186 A | 5/1981 | Loveless et al. |
| 4,311,137 A * | 1/1982 | Gerard .............. A61M 25/0606 604/122 |
| 4,317,445 A | 3/1982 | Robinson |
| 4,326,519 A | 4/1982 | D'Alo et al. |
| 4,353,369 A | 10/1982 | Muetterties et al. |
| 4,362,156 A | 12/1982 | Feller, Jr. et al. |
| 4,365,630 A | 12/1982 | McFarlane |
| 4,387,879 A | 6/1983 | Tauschinski |
| 4,419,094 A | 12/1983 | Patel |
| 4,445,893 A | 5/1984 | Bodicky |
| 4,449,693 A | 5/1984 | Gereg |
| 4,496,348 A | 1/1985 | Genese et al. |
| 4,525,157 A | 6/1985 | Vaillancourt |
| 4,531,935 A | 7/1985 | Berryessa |
| 4,682,980 A | 7/1987 | Suzuki |
| 4,701,162 A | 10/1987 | Rosenberg |
| 4,703,761 A | 11/1987 | Rathbone et al. |
| 4,758,225 A | 7/1988 | Cox et al. |
| 4,765,588 A | 8/1988 | Atkinson |
| 4,772,264 A | 9/1988 | Cragg |
| 4,813,939 A | 3/1989 | Marcus |
| 4,834,708 A | 5/1989 | Pillari |
| 4,842,591 A | 6/1989 | Luther |
| 4,874,377 A | 10/1989 | Newgard et al. |
| 4,894,052 A | 1/1990 | Crawford |
| 4,917,668 A | 4/1990 | Haindl |
| 4,917,671 A | 4/1990 | Chang |
| 4,925,444 A | 5/1990 | Orkin et al. |
| 4,935,010 A | 6/1990 | Cox et al. |
| 4,950,257 A | 8/1990 | Hibbs et al. |
| 4,966,586 A | 10/1990 | Vaillancourt |
| D315,822 S | 3/1991 | Ryan |
| 5,032,116 A | 7/1991 | Peterson et al. |
| 5,041,097 A | 8/1991 | Johnson |
| 5,053,014 A | 10/1991 | Van Heugten |
| 5,057,087 A | 10/1991 | Harmon |
| 5,059,186 A | 10/1991 | Yamamoto et al. |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,135,504 A | 8/1992 | McLees |
| 5,154,703 A | 10/1992 | Bonaldo |
| 5,156,596 A | 10/1992 | Balbierz et al. |
| 5,176,653 A | 1/1993 | Metals |
| 5,176,662 A | 1/1993 | Bartholomew et al. |
| 5,201,717 A | 4/1993 | Wyatt et al. |
| 5,211,634 A | 5/1993 | Vaillancourt |
| 5,215,525 A | 6/1993 | Sturman |
| 5,215,528 A | 6/1993 | Purdy et al. |
| 5,215,529 A | 6/1993 | Fields et al. |
| 5,226,883 A | 7/1993 | Katsaros et al. |
| 5,234,410 A | 8/1993 | Graham et al. |
| 5,242,411 A | 9/1993 | Yamamoto et al. |
| 5,254,097 A | 10/1993 | Schock et al. |
| 5,267,971 A | 12/1993 | Brimhall |
| 5,269,764 A | 12/1993 | Vetter et al. |
| 5,273,546 A | 12/1993 | McLaughlin et al. |
| 5,290,222 A | 3/1994 | Feng et al. |
| 5,290,246 A | 3/1994 | Yamamoto et al. |
| 5,295,969 A | 3/1994 | Fischell et al. |
| 5,306,243 A | 4/1994 | Bonaldo |
| 5,312,359 A | 5/1994 | Wallace |
| 5,328,482 A | 7/1994 | Sircom et al. |
| 5,330,435 A | 7/1994 | Vaillancourt |
| 5,342,315 A | 8/1994 | Rowe et al. |
| 5,350,363 A | 9/1994 | Goode et al. |
| 5,352,205 A | 10/1994 | Dales et al. |
| 5,354,281 A | 10/1994 | Chen |
| 5,356,381 A | 10/1994 | Ensminger et al. |
| 5,368,029 A | 11/1994 | Holcombe et al. |
| 5,405,323 A | 4/1995 | Rogers et al. |
| 5,447,501 A | 9/1995 | Karlsson et al. |
| 5,456,675 A | 10/1995 | Wolbring et al. |
| 5,458,658 A | 10/1995 | Sircom |
| 5,487,728 A | 1/1996 | Vaillancourt |
| 5,498,241 A | 3/1996 | Fabozzi |
| 5,509,912 A | 4/1996 | Vaillancourt et al. |
| 5,520,666 A | 5/1996 | Choudhury et al. |
| 5,542,932 A | 8/1996 | Daugherty |
| 5,549,566 A | 8/1996 | Elias et al. |
| 5,549,576 A | 8/1996 | Patterson et al. |
| 5,549,577 A | 8/1996 | Siegel et al. |
| 5,562,631 A | 10/1996 | Bogert |
| 5,562,633 A | 10/1996 | Wozencroft |
| 5,573,510 A | 11/1996 | Isaacson |
| 5,575,769 A | 11/1996 | Vaillancourt |
| 5,575,777 A | 11/1996 | Cover et al. |
| 5,584,809 A | 12/1996 | Gaba |
| 5,599,310 A | 2/1997 | Bogert |
| 5,601,536 A | 2/1997 | Crawford et al. |
| 5,613,663 A | 3/1997 | Schmidt et al. |
| 5,651,772 A | 7/1997 | Arnett |
| 5,657,963 A | 8/1997 | Hinchliffe et al. |
| 5,676,656 A | 10/1997 | Brimhall |
| 5,690,612 A | 11/1997 | Lopez et al. |
| 5,690,619 A | 11/1997 | Erskine |
| 5,697,907 A | 12/1997 | Gaba |
| 5,697,914 A | 12/1997 | Brimhall |
| 5,697,915 A | 12/1997 | Lynn |
| 5,699,821 A | 12/1997 | Paradis |
| 5,700,244 A | 12/1997 | Kriesel |
| 5,700,250 A | 12/1997 | Erskine |
| 5,704,919 A | 1/1998 | Kraus et al. |
| 5,718,688 A | 2/1998 | Wozencroft |
| 5,730,123 A | 3/1998 | Lorenzen et al. |
| 5,738,144 A | 4/1998 | Rogers |
| 5,749,856 A | 5/1998 | Zadini et al. |
| 5,749,861 A | 5/1998 | Guala et al. |
| 5,772,636 A | 6/1998 | Brimhall et al. |
| 5,800,399 A | 9/1998 | Bogert et al. |
| 5,806,831 A | 9/1998 | Paradis |
| 5,810,780 A | 9/1998 | Brimhall et al. |
| 5,817,069 A | 10/1998 | Arnett |
| 5,843,046 A | 12/1998 | Motisi et al. |
| 5,853,393 A | 12/1998 | Bogert |
| 5,882,345 A | 3/1999 | Yoon |
| 5,911,710 A | 6/1999 | Barry et al. |
| 5,935,109 A | 8/1999 | Donnan |
| 5,935,110 A | 8/1999 | Brimhall |
| 5,947,932 A | 9/1999 | Desecki et al. |
| 5,954,698 A | 9/1999 | Pike |
| 5,961,497 A | 10/1999 | Larkin |
| 5,967,490 A | 10/1999 | Pike |
| 6,039,302 A | 3/2000 | Cote, Sr. et al. |
| 6,056,726 A | 5/2000 | Isaacson |
| 6,077,244 A | 6/2000 | Botich et al. |
| 6,117,108 A | 9/2000 | Woehr et al. |
| 6,142,981 A | 11/2000 | Heck et al. |
| 6,156,010 A | 12/2000 | Kuracina et al. |

(56) References Cited

U.S. PATENT DOCUMENTS

| | | |
|---|---|---|
| 6,171,287 B1 | 1/2001 | Lynn et al. |
| 6,206,851 B1 | 3/2001 | Prosl |
| 6,221,047 B1 | 4/2001 | Greene et al. |
| 6,224,569 B1 | 5/2001 | Brimhall |
| 6,273,869 B1 | 8/2001 | Vaillancourt |
| 6,287,278 B1 | 9/2001 | Woehr et al. |
| D451,599 S | 12/2001 | Crawford et al. |
| D451,600 S | 12/2001 | Crawford et al. |
| 6,379,332 B1 | 4/2002 | Van Landuyt |
| D458,678 S | 6/2002 | Cindrich |
| D458,994 S | 6/2002 | Cindrich |
| 6,440,119 B1 | 8/2002 | Nakada et al. |
| 6,461,362 B1 | 10/2002 | Halseth et al. |
| 6,485,473 B1 | 11/2002 | Lynn |
| 6,497,994 B1 * | 12/2002 | Kafrawy ............ C23F 1/02 163/5 |
| 6,506,181 B2 | 1/2003 | Meng et al. |
| D469,870 S | 2/2003 | Niermann et al. |
| 6,565,542 B2 | 5/2003 | Kumar |
| 6,575,960 B2 | 6/2003 | Becker et al. |
| 6,595,954 B1 | 7/2003 | Luther et al. |
| 6,595,981 B2 | 7/2003 | Huet |
| 6,616,630 B1 | 9/2003 | Woehr et al. |
| 6,652,486 B2 | 11/2003 | Bialecki et al. |
| 6,663,592 B2 | 12/2003 | Rhad et al. |
| 6,689,102 B2 | 2/2004 | Greene |
| 6,695,814 B2 | 2/2004 | Greene et al. |
| 6,699,221 B2 | 3/2004 | Vaillancourt |
| 6,709,419 B2 | 3/2004 | Woehr |
| 6,719,726 B2 | 4/2004 | Meng et al. |
| 6,740,063 B2 | 5/2004 | Lynn |
| D491,266 S | 6/2004 | Cindrich et al. |
| D492,031 S | 6/2004 | Cindrich et al. |
| 6,749,588 B1 | 6/2004 | Howell et al. |
| D492,774 S | 7/2004 | Cindrich et al. |
| 6,837,884 B2 | 1/2005 | Woloszko |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| D592,302 S | 5/2009 | Stokes et al. |
| 7,670,317 B2 | 3/2010 | Cindrich et al. |
| 7,694,403 B2 | 4/2010 | Moulton |
| 7,736,339 B2 | 6/2010 | Woehr et al. |
| 7,905,856 B2 | 3/2011 | McGuckin, Jr. et al. |
| 7,914,494 B2 | 3/2011 | Hiejima |
| 8,066,670 B2 | 11/2011 | Cluff et al. |
| 8,066,675 B2 | 11/2011 | Cindrich et al. |
| 8,070,725 B2 | 12/2011 | Christensen |
| 8,357,119 B2 | 1/2013 | Stout et al. |
| 8,361,020 B2 | 1/2013 | Stout et al. |
| 8,388,583 B2 | 3/2013 | Stout et al. |
| 8,574,203 B2 | 11/2013 | Stout et al. |
| 8,597,252 B2 | 12/2013 | Burkholz et al. |
| 8,641,675 B2 | 2/2014 | Stout et al. |
| 8,679,063 B2 | 3/2014 | Stout et al. |
| D713,522 S | 9/2014 | Woehr et al. |
| D819,802 S | 6/2018 | Burkholz et al. |
| D835,262 S | 12/2018 | Burkholz et al. |
| D837,368 S | 1/2019 | Burkholz et al. |
| 2001/0053895 A1 | 12/2001 | Vaillancourt |
| 2002/0072712 A1 | 6/2002 | Nool et al. |
| 2002/0082546 A1 | 6/2002 | Crank et al. |
| 2002/0177814 A1 | 11/2002 | Meng et al. |
| 2003/0083620 A1 | 5/2003 | Luther et al. |
| 2004/0078003 A1 | 4/2004 | Smith et al. |
| 2004/0092889 A1 | 5/2004 | Ferguson et al. |
| 2004/0102735 A1 | 5/2004 | Moulton et al. |
| 2004/0181192 A1 | 9/2004 | Cuppy |
| 2004/0193112 A1 | 9/2004 | Glazier et al. |
| 2004/0204681 A1 | 10/2004 | Thoresen et al. |
| 2004/0225260 A1 | 11/2004 | Villa et al. |
| 2004/0243060 A1 | 12/2004 | Rossi et al. |
| 2004/0243061 A1 | 12/2004 | McGurk |
| 2005/0273019 A1 | 12/2005 | Conway et al. |
| 2005/0277879 A1 | 12/2005 | Daga |
| 2006/0163515 A1 | 7/2006 | Ruschke |
| 2007/0043334 A1 | 2/2007 | Guala |
| 2007/0083157 A1 | 4/2007 | Belley et al. |
| 2007/0083162 A1 | 4/2007 | O'Reagan et al. |
| 2007/0093778 A1 | 4/2007 | Cindrich et al. |
| 2007/0191777 A1 | 8/2007 | King |
| 2007/0225648 A1 | 9/2007 | Winsor et al. |
| 2007/0233007 A1 | 10/2007 | Adams |
| 2008/0039796 A1 | 2/2008 | Nakajima |
| 2008/0108944 A1 | 5/2008 | Woehr et al. |
| 2008/0132832 A1 | 6/2008 | McKinnon et al. |
| 2008/0167577 A1 * | 7/2008 | Weilbacher ........ A61B 5/15003 600/576 |
| 2008/0255473 A1 | 10/2008 | Dalebout et al. |
| 2008/0287906 A1 | 11/2008 | Burkholz et al. |
| 2009/0054845 A1 | 2/2009 | Puhasmagi et al. |
| 2009/0099431 A1 | 4/2009 | Dalebout et al. |
| 2009/0287189 A1 | 11/2009 | Suwito |
| 2010/0204648 A1 | 8/2010 | Stout et al. |
| 2010/0204675 A1 | 8/2010 | Woehr et al. |
| 2010/0222746 A1 | 9/2010 | Burkholz |
| 2010/0280455 A1 | 11/2010 | Ogawa et al. |
| 2011/0046570 A1 | 2/2011 | Stout et al. |
| 2011/0054403 A1 | 3/2011 | Tanabe et al. |
| 2011/0130728 A1 | 6/2011 | McKinnon |
| 2012/0016265 A1 | 1/2012 | Peterson et al. |
| 2012/0016307 A1 | 1/2012 | Burkholz et al. |
| 2012/0053523 A1 | 3/2012 | Harding |
| 2013/0090608 A1 | 4/2013 | Stout et al. |
| 2013/0218082 A1 | 8/2013 | Hyer et al. |
| 2013/0237925 A1 | 9/2013 | Trainer et al. |
| 2014/0046258 A1 | 2/2014 | Stout et al. |
| 2014/0107584 A1 | 4/2014 | Rosenberg et al. |
| 2014/0364809 A1 | 12/2014 | Isaacson et al. |
| 2015/0224296 A1 | 8/2015 | Winsor |
| 2017/0120008 A1 | 5/2017 | Burkholz et al. |
| 2017/0120014 A1 | 5/2017 | Harding et al. |
| 2017/0216535 A1 | 8/2017 | Mao |
| 2017/0347913 A1 | 12/2017 | Isaacson et al. |

FOREIGN PATENT DOCUMENTS

| | | |
|---|---|---|
| CN | 102440822 A | 5/2012 |
| CN | 102716541 A | 10/2012 |
| CN | 203852671 | 10/2014 |
| DE | 20 2009 009 602 U1 | 12/2009 |
| EP | D 268 480 A1 | 5/1988 |
| EP | 0 732 120 A1 | 9/1996 |
| EP | 0 812 601 A2 | 12/1997 |
| EP | 0 993 839 A1 | 4/2000 |
| EP | 1 679 043 A1 | 7/2006 |
| EP | 1 884 257 A1 | 2/2008 |
| EP | 1 944 049 A1 | 7/2008 |
| EP | 2022421 | 2/2009 |
| EP | 2 044 970 A1 | 4/2009 |
| EP | 2 327 434 A1 | 6/2011 |
| GB | 2508466 A | 6/2014 |
| JP | S56102253 | 8/1981 |
| JP | S5832774 | 2/1983 |
| JP | H06-086821 | 3/1994 |
| JP | H09-509075 | 9/1997 |
| JP | 2000279270 | 10/2000 |
| JP | 2004528127 | 9/2004 |
| JP | 2011045544 | 3/2011 |
| JP | 2012521796 | 9/2012 |
| JP | 2012200425 | 10/2012 |
| JP | 3188771 | 1/2014 |
| JP | 2014108112 | 6/2014 |
| WO | 88/07388 A1 | 10/1988 |
| WO | 97/45151 | 12/1997 |
| WO | 98/42393 A1 | 10/1998 |
| WO | 99/34849 A1 | 7/1999 |
| WO | 01/12254 A1 | 2/2001 |
| WO | 02/096495 | 12/2002 |
| WO | 2004/032995 A2 | 4/2004 |
| WO | 2004/082727 | 9/2004 |
| WO | 2004/087247 | 10/2004 |

(56) References Cited

FOREIGN PATENT DOCUMENTS

| | | |
|---|---|---|
| WO | 2004/098685 A1 | 11/2004 |
| WO | 2006/037638 A1 | 4/2006 |
| WO | 2007/052655 | 5/2007 |
| WO | 2008/022258 A2 | 2/2008 |
| WO | 2008/045761 A2 | 4/2008 |
| WO | 2008/052790 A2 | 5/2008 |
| WO | 2008/058132 A2 | 5/2008 |
| WO | 2008/058133 A2 | 5/2008 |
| WO | 2009/114833 A1 | 9/2009 |
| WO | 2010/093791 A1 | 8/2010 |
| WO | 2010/111283 | 9/2010 |
| WO | 2010/111285 A1 | 9/2010 |
| WO | 2011/055287 | 5/2011 |
| WO | 2011/109542 A1 | 9/2011 |
| WO | 2016/007442 | 1/2016 |
| WO | 2017/062579 | 4/2017 |

* cited by examiner

CLOSED IV ACCESS DEVICE WITH PADDLE GRIP NEEDLE HUB AND FLASH CHAMBER

RELATED APPLICATIONS

This application claims the benefit of U.S. Provisional Patent Application No. 62/247,617, which was filed on Oct. 28, 2015, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND

When an IV access device is identified as being "closed" or "integrated," it generally refers to the fact that the device is configured to prevent blood from escaping the device during insertion of the catheter. Typically, such IV access devices accomplish this by integrating an extension set with the catheter adapter.

FIG. 1 illustrates an example of a prior art closed IV access device 100. Device 100 includes a catheter adapter 101 from which a catheter 101*a* extends, a needle hub 102 from which a needle 102*a* extends, an extension tube 103 that is coupled to catheter adapter 101 at one end and includes a Y-adapter 104 coupled to the other end, and a clamp 107 for blocking or limiting fluid flow through extension tube 103. Y-adapter 104 includes a port 105 and a vent plug 106. Device 100 can be a closed system by incorporating fluid flow blocking components (e.g., a septum or vent) into each external opening of the device such as into a proximal end of catheter adapter 101 and into any ports in adapter 104.

To facilitate proper insertion of the needle in a closed system, it is typical for the needle to include a flashback notch towards its distal end. This flashback notch is oftentimes positioned within the catheter so that blood flowing out through the flashback notch will be visible within the catheter. When blood is seen flowing through the flashback notch, the clinician can know that the needle tip is contained within a vein. However, a flashback notch alone may not be sufficient to provide confirmation of proper catheter placement. For example, even if the needle tip is contained within the vein, the tip of the catheter may not be. Also, during needle withdrawal, it is possible that the catheter tip may be displaced from within the vein.

For these reasons, closed IV access devices oftentimes are configured to allow blood to flow into the extension tube to provide a secondary confirmation of proper catheter placement. For example, access device 100 may include a vent plug that is coupled to a port of luer adapter 104. The vent plug can allow air to escape from extension tube 103 thereby allowing the patient's blood pressure to cause blood to flow into extension tube 103. If blood flows into extension tube 103, the clinician can know that the tip of catheter 101*a* is properly positioned within the patient's vein.

Although using the extension tube of a closed system is an effective way of providing secondary confirmation of proper catheter placement, some catheter insertion techniques prevent it from being used. For example, it is common in some countries to prime extension tube 103 with saline solution prior to inserting catheter 101*a*. In such cases, because extension tube 103 will be filled with saline during catheter insertion, blood will not flow into extension tube 103 to provide the secondary confirmation.

BRIEF SUMMARY OF THE INVENTION

The present invention is generally directed to a closed IV access device that is configured to provide secondary confirmation of proper catheter placement without requiring blood to flow into the extension tube. Although a closed IV access device in accordance with the present invention can be of primary benefit in instances where the extension tube is pre-primed with saline solution, the present invention may also be employed when the extension tube is not primed.

An IV access device can include a needle hub that incorporates a flash chamber. The flash chamber can be used to provide visual confirmation of proper catheter placement within a vein. The flash chamber can include a path-defining structure to facilitate identifying whether blood is continually flowing into the flash chamber. The flash chamber may also be removable from the needle hub. In some cases, the needle hub may include a paddle grip that facilitates insertion of the catheter and separation of the needle hub from the catheter adapter.

In one embodiment, the present invention is implemented as an IV access device that includes a catheter adapter from which a catheter extends distally; an extension tube coupled to the catheter adapter; and a needle hub from which a needle extends distally. The needle hub is coupled to the catheter adapter such that the needle extends through the catheter. The needle hub further includes a flash chamber that is in fluid communication with a lumen of the needle thereby allowing blood to flow into the flash chamber when a distal tip of the needle is contained within a patient's vein.

In another embodiment, the present invention is implemented as an IV access device that includes a catheter adapter from which a catheter extends distally; an extension tube coupled to the catheter adapter; and a needle hub from which a needle extends distally. The needle hub is coupled to the catheter adapter such that the needle extends through the catheter. The needle hub includes a flash chamber, a proximal end of the needle forming a fluid pathway for blood to flow into the flash chamber. The flash chamber includes a plug that vents air but blocks the flow of blood thereby allowing blood to flow into the flash chamber when a distal tip of the needle is contained within a patient's vein.

In another embodiment, the present invention is implemented as an IV access device comprising a catheter adapter having a wing and a catheter that extends distally; an extension tube that is coupled to the catheter adapter; and a needle hub that includes a paddle grip, a needle that extends through the catheter when the needle hub is coupled to the catheter adapter, and a flash chamber. A proximal end of the needle provides a fluid pathway for blood to flow into the flash chamber when a distal tip of the needle is contained within a patient's vein.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Figure 1:
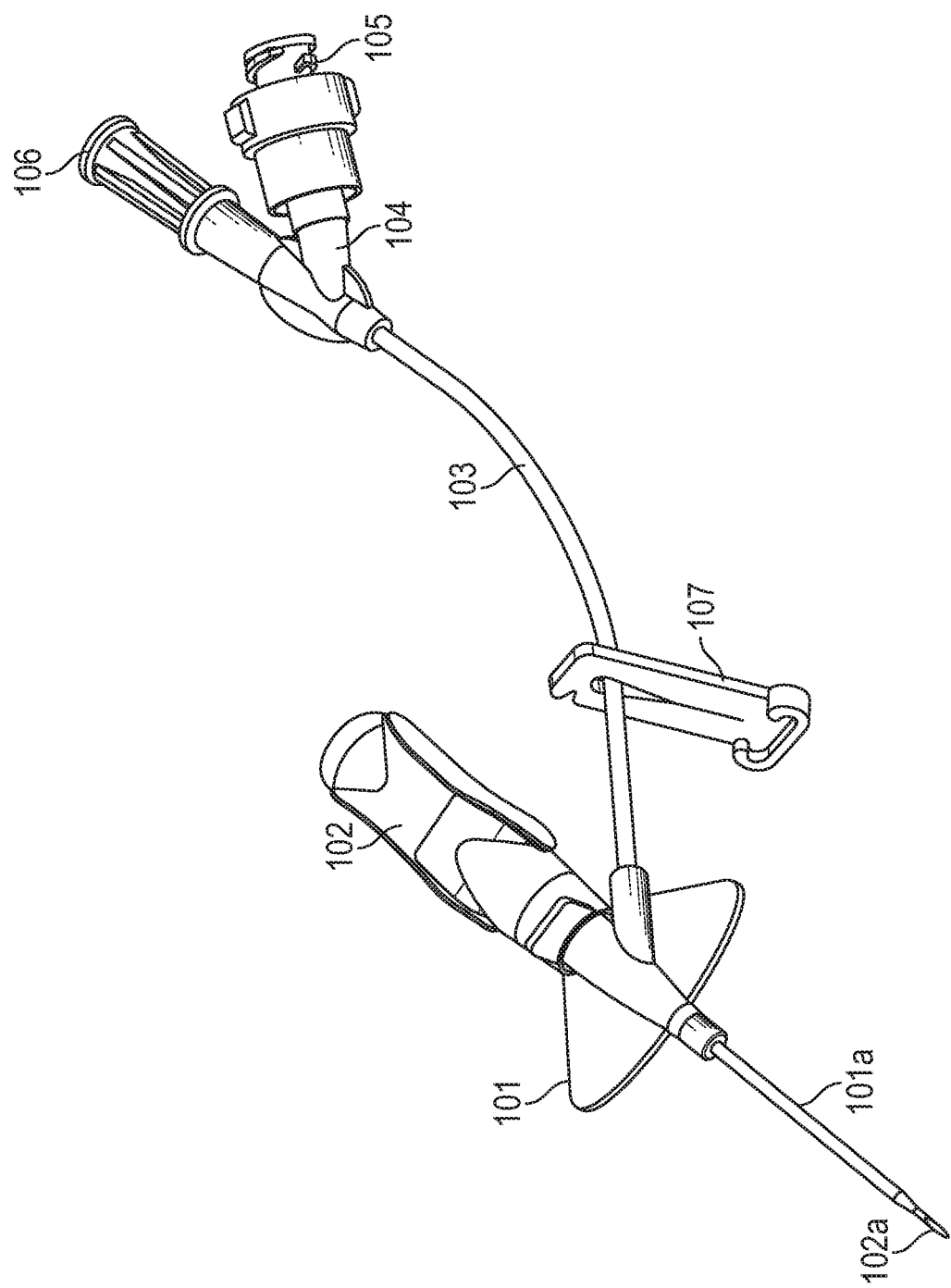
FIG. 1 illustrates a prior art closed IV access device.
Figure 2:
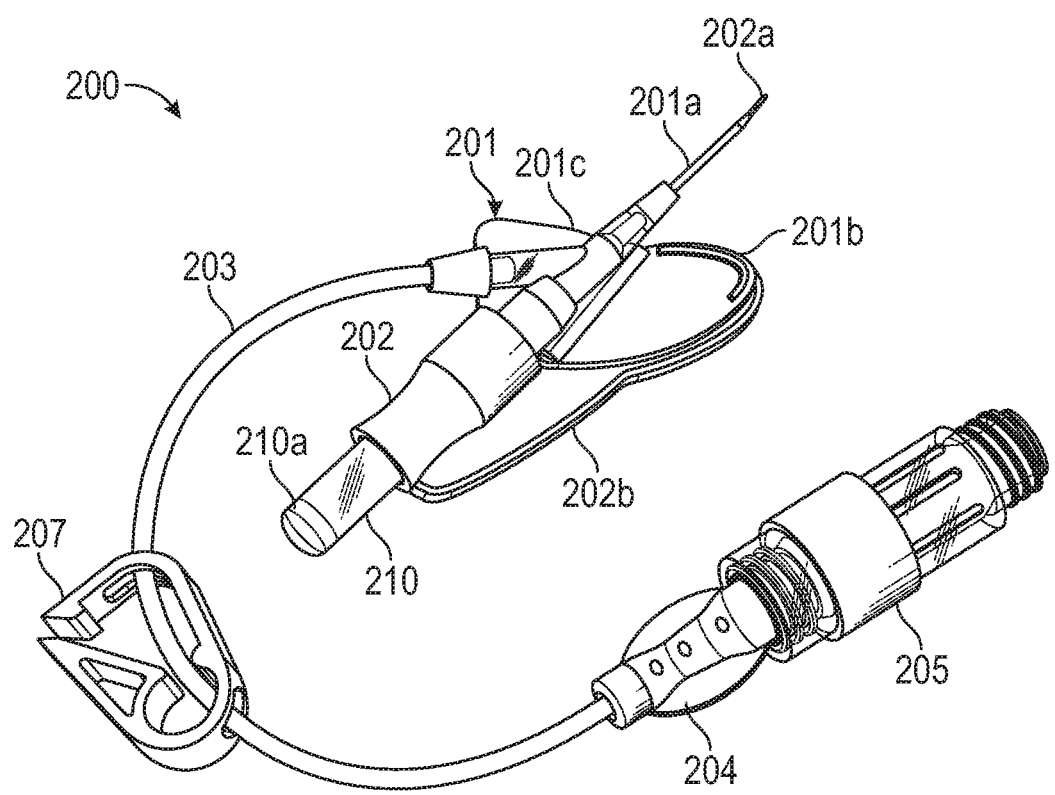
FIG. 2 illustrates a closed IV access device in accordance with one or more embodiments of the present invention.

FIG. 2 illustrates an example of a closed IV access device 200 that is configured in accordance with one or more embodiments of the present invention. Access device 200 includes a catheter adapter 201 from which a catheter 201a extends distally, a needle hub 202 from which a needle 202a extends distally, an extension tube 203 that is fluidly coupled to a lumen of catheter adapter 201, and a clamp 207 for restricting the flow of fluid through extension tube 203. A luer adapter 204 or other type of adapter can be coupled to the end of extension tube 203. Also, a luer access device 205, such as one that includes a septum, may be coupled to luer adapter 204.

Catheter adapter 201 can include a stabilization platform formed by wings 201b and 201c which extend outwardly from opposite sides of catheter adapter 201. As shown in FIG. 2, access device 200 is configured for right-hand use in that extension tube 203 couples to the left side of catheter adapter 201 such that wing 201b is fully exposed. This can facilitate gripping wing 201b with the thumb of the right hand. In some embodiments, an interface for coupling extension tube 203 to catheter adapter 201 can be formed into wing 201c. Of course, in an access device designed for left-hand use, wings 201b, 201c and extension tube 203 would be on opposite sides of catheter adapter 201 from what is shown in FIG. 2.

Needle hub 202 includes a paddle grip 202b that extends outwardly from the right side of needle hub 202 and has a shape that generally corresponds to the shape of wing 201b. Accordingly, paddle grip 202b can be positioned directly beneath wing 201b so that wing 201b and paddle grip 202b can be sandwiched between the clinician's thumb and index finger during insertion of catheter 201a. By configuring paddle grip 202b in this manner, the clinician can easily withdraw needle hub 202 from catheter adapter 201 by simply sliding the index finger backwards with respect to the thumb thereby causing the paddle grip 202b to slide backward away from wing 201b.

Figure 3:
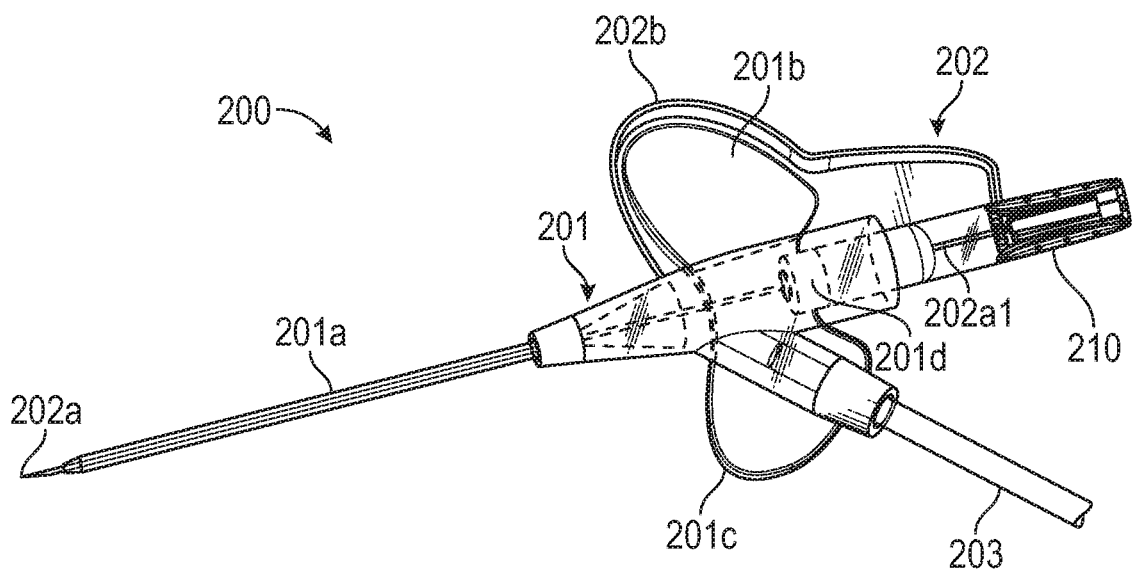
FIG. 3 also illustrates a closed IV access device in accordance with one or more embodiments of the present invention.

Needle hub 202 also includes a flash chamber 210 that is coupled to the proximal end of needle hub 202. As is better shown in FIG. 3, flash chamber 210 can include a porous vent plug 210a that allows air to escape through a proximal opening in needle hub 202 while preventing blood from escaping. Alternatively, flash chamber 210 could include different means for venting air but blocking blood including, e.g., a membrane, filter paper, woven or non-woven material, a plug that includes venting channels along an interface between the proximal end of needle hub 202 and the plug, etc. Also, a proximal end of needle 202a can extend into flash chamber 210 and can include an opening 202a1 to allow blood to flow out of needle 202a and into flash chamber 210.

Needle 202a can include a notch (not shown) towards its distal end for providing flashback. The flashback provided through this notch can provide a primary confirmation that catheter 201a has been properly placed within a vein.

Additionally, flash chamber 210 can provide secondary confirmation that catheter 201a is properly positioned within the vein. In particular, because the proximal end of needle 202a opens into flash chamber 210 and because flash chamber is vented to the external environment via plug 210a, when the distal end of needle 202a is properly positioned within a vein, the patient's blood pressure will cause blood to flow into flash chamber 210. Because this flow of blood into flashback chamber 210 is accomplished via needle 202a, this secondary confirmation can be obtained even if extension tube 203 is primed with saline prior to insertion of catheter 201a.

Once the clinician has determined that catheter 201a has been properly placed, needle hub 202 can be withdrawn from catheter adapter 201 by simply sliding paddle grip 202b backwards away from wing 201b. Catheter adapter 201 can include a septum 201d through which needle 202a can extend. Septum 201d can reseal after withdrawal of needle 202a to prevent any fluid from escaping out through the proximal opening of catheter adapter 201.

Figure 4:
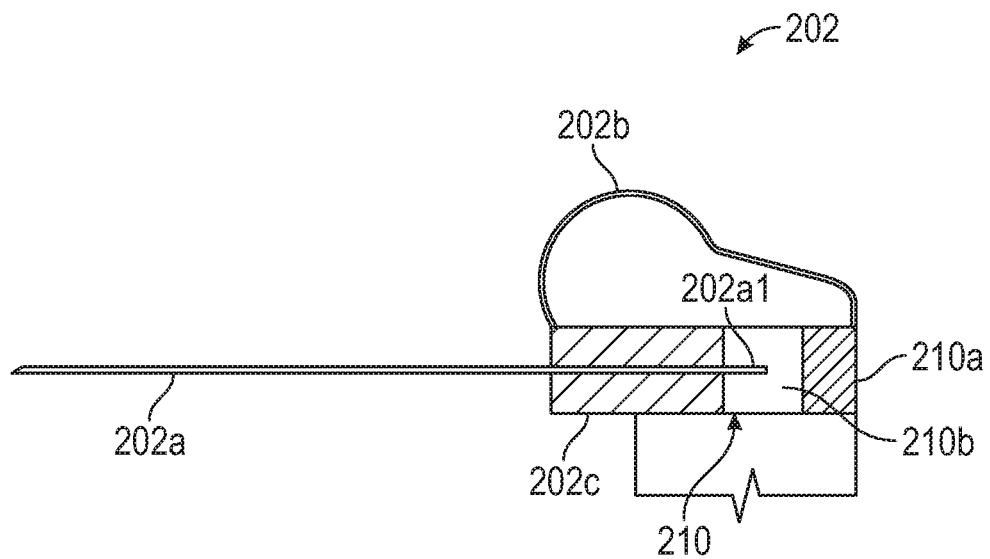
FIG. 4 illustrates a cross-sectional view of an example needle hub that includes a flash chamber in accordance with one or more embodiments of the present invention.

FIG. 4 provides a cross-sectional view of one embodiment of needle hub 202. As shown, needle hub 202 can include a needle retaining portion 202c through which needle 202a extends. Needle retaining portion 202c can be configured to secure needle 202a to needle hub 202 in any suitable manner such as via an adhesive or a friction fit. In some embodiments, needle retaining portion 202c can be configured to insert within a proximal opening of catheter adapter 201 to secure needle hub 202 to catheter adapter 201.

Flash chamber 210 generally comprises plug 210a and a chamber 210b. Opening 202a1 of needle 202a can be positioned within chamber 210b so that blood may flow into and accumulate within chamber 210b. Plug 210a can be positioned between chamber 210b and the external environment to allow air to be vented from chamber 210b as blood flows towards and into chamber 210b.

In some embodiments, the dimension of a lumen of needle 202a may be configured to cause blood to flow into chamber 210b at a particular rate. For example, it may be desirable to limit the flow of blood into chamber 210b so that chamber 210b will not become full until catheter 201a has been positioned within a vein for a specified amount of time. In some cases, this specified amount of time may be as long as 20 seconds. Accordingly, one or more dimensions of the fluid pathway through needle 202a can be configured to provide a desired flowrate. Alternatively or additionally, plug 210a may be configured to vent air at a specified rate to limit the flowrate of blood into chamber 210b.

In some cases, however, it may be difficult for the clinician to determine whether blood is continually flowing into chamber 210b. For example, if catheter 201a were initially placed within the vein thereby causing blood to flow into chamber 210b, but was then positioned outside the vein, it may be difficult for the clinician to determine that blood is no longer flowing into chamber 210b. This may be especially true when needle 202a is configured to provide a slow flowrate into chamber 210b. To address this issue, flash chamber 210 can be configured to include a path-defining structure.

Figure 5:
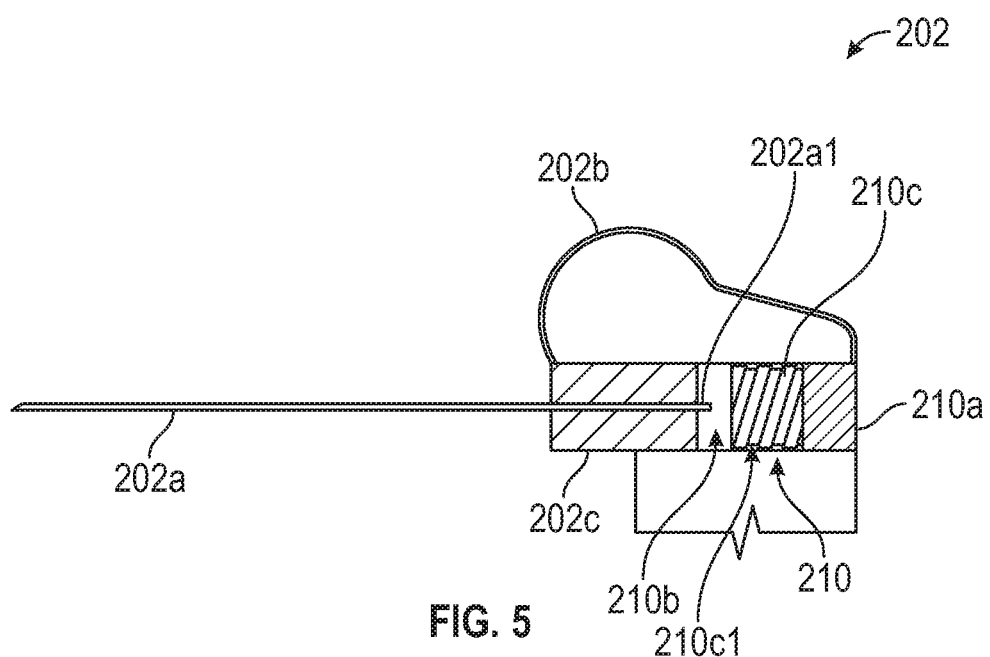
FIG. 5 illustrates a cross-sectional view of an example needle hub that includes a flash chamber having a path-defining structure in accordance with one or more embodiments of the present invention.

FIG. 5 illustrates an example of a path-defining structure 210c that can be incorporated into flash chamber 210. It is noted that FIG. 5 depicts a cross-sectional view of needle hub 202 with path-defining structure 210c not being shown as a cross-section so that the outer surface of the path-defining structure can be seen. As in FIG. 4, flash chamber 210 includes a chamber 210b in which opening 202a1 of needle 202a is contained. Path-defining structure 210c is positioned between plug 210a and opening 202a1 and includes a pathway 210c1 through which blood can flow. In particular, pathway 210c1 extends around the outer surface of path-defining structure 210c. The outer diameter of path-defining structure 210c can be substantially the same as the inside diameter of flash chamber 210 such that blood is confined to flowing through pathway 210c1 to reach plug 210a.

Pathway 210c1 can function to increase the distance that blood can flow within flash chamber 210. Because pathway 210c1 can have smaller cross-sectional dimensions than chamber 210b, it will be easier to detect the flow of blood into flash chamber 210. In particular, by including path-defining structure 210c, the clinician will be able to easily see the blood advance along pathway 210c1 towards plug 210a. As long as the blood continues to advance along pathway 210c1, the clinician can know that catheter 201a is likely positioned correctly.

In this example, pathway 210c1 is shown as having a spiral shape; however, path-defining structure 210c can include any suitably-shaped pathway. Also, although FIG. 5 illustrates that flash chamber 210 includes a chamber 210b that is separate from pathway 210c1 (i.e., that path-defining structure 210c is spaced from needle retaining portion 202c), in some embodiments, path-defining structure 210c may be configured such that pathway 210c1 extends overtop the proximal end of needle 202a so that blood flows directly into pathway 210c1 rather than flowing first into chamber 210b.

Further, in some embodiments, path-defining structure 210c and needle retaining portion 202c can be the same structural component. However, using a separately-formed path-defining structure 210c may be preferred in many cases since it facilitates the manufacture of needle hub 202. For example, needle hub 202 could be molded with a proximal opening into which a separately formed path-defining structure 210c and plug 210a could be inserted.

Figure 6:
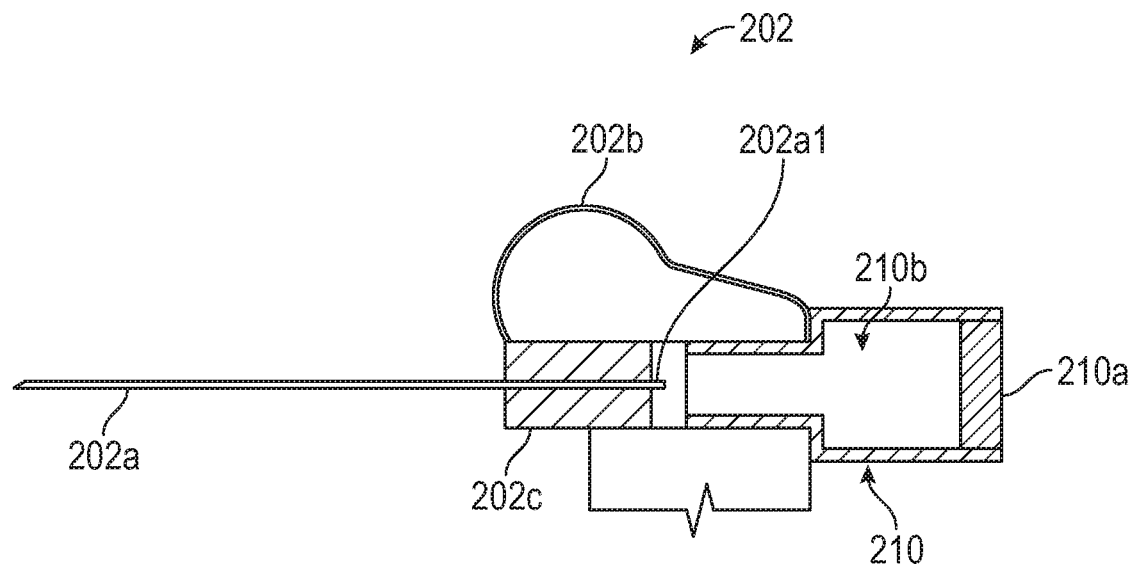
FIG. 6 illustrates a cross-sectional view of an example needle hub that includes a flash chamber that is removable in accordance with one or more embodiments of the present invention.
Figure 7:
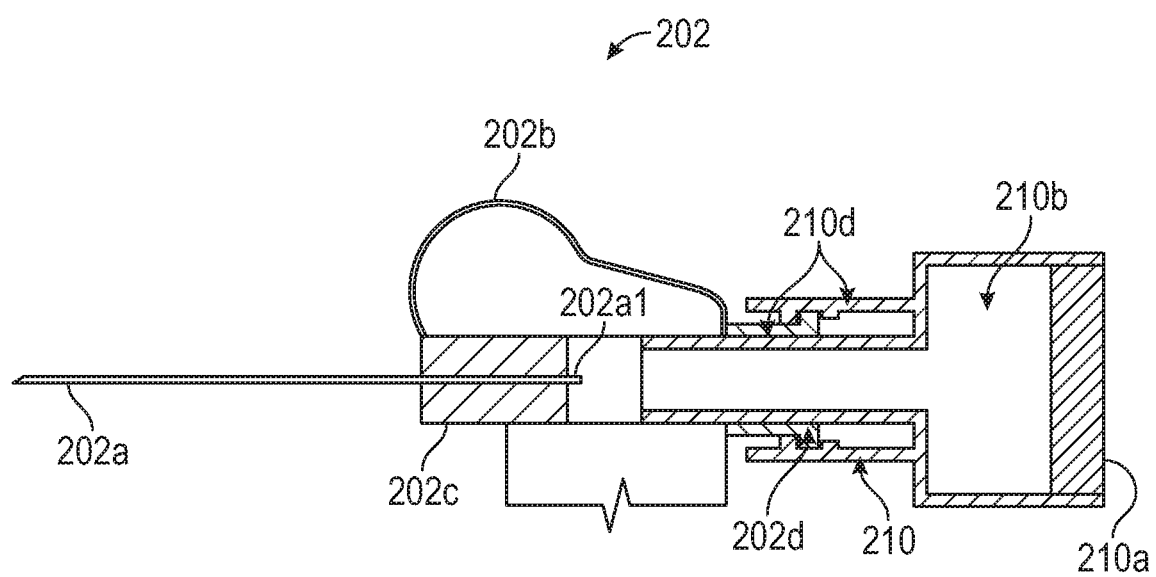
FIG. 7 illustrates a cross-sectional view of an example needle hub that includes a flash chamber that is removable in accordance with one or more embodiments of the present invention.

In some embodiments, flash chamber 210 can be configured to be removable from needle hub 202. FIGS. 6 and 7 each illustrate examples of how this can be accomplished. In FIG. 6, and as described above, flash chamber 210 forms chamber 210b and contains plug 210a. Additionally, flash chamber 210 is configured with a distal end that removably inserts into a proximal opening of needle hub 202. In this configuration, after chamber 210b has been filled with blood and needle hub 202 has been separated from catheter adapter 201, flash chamber 210 can be pulled out from needle hub 202. A distal opening of flash chamber 210 can be configured to prevent the blood from escaping chamber 210b until a desired time. For example, the size of the distal opening of flash chamber 210 can be sufficiently small to prevent the blood from escaping until the body of flash chamber 210 is squeezed. In this way, flash chamber 210 could be employed to perform point-of-care testing on the blood.

In FIG. 7, flash chamber 210 is also configured to be removable. However, in contrast to FIG. 6, needle hub 202 includes a female luer port 202d and flash chamber 210 includes a male luer lock coupling 210d to allow flash chamber 210 to be coupled to port 202d. Coupling 210d could alternatively be configured as a male luer slip coupling. Flash chamber 210 could be used in a similar manner as described above with respect to FIG. 6. Additionally, because needle hub 202 includes a female luer port 202d, prior to removing needle hub 202 from catheter adapter 201, flash chamber 210 could be removed to allow a separate device, such as a blood collection holder, to be connected to female luer port 202d to collect larger blood samples.

Figure 8A:
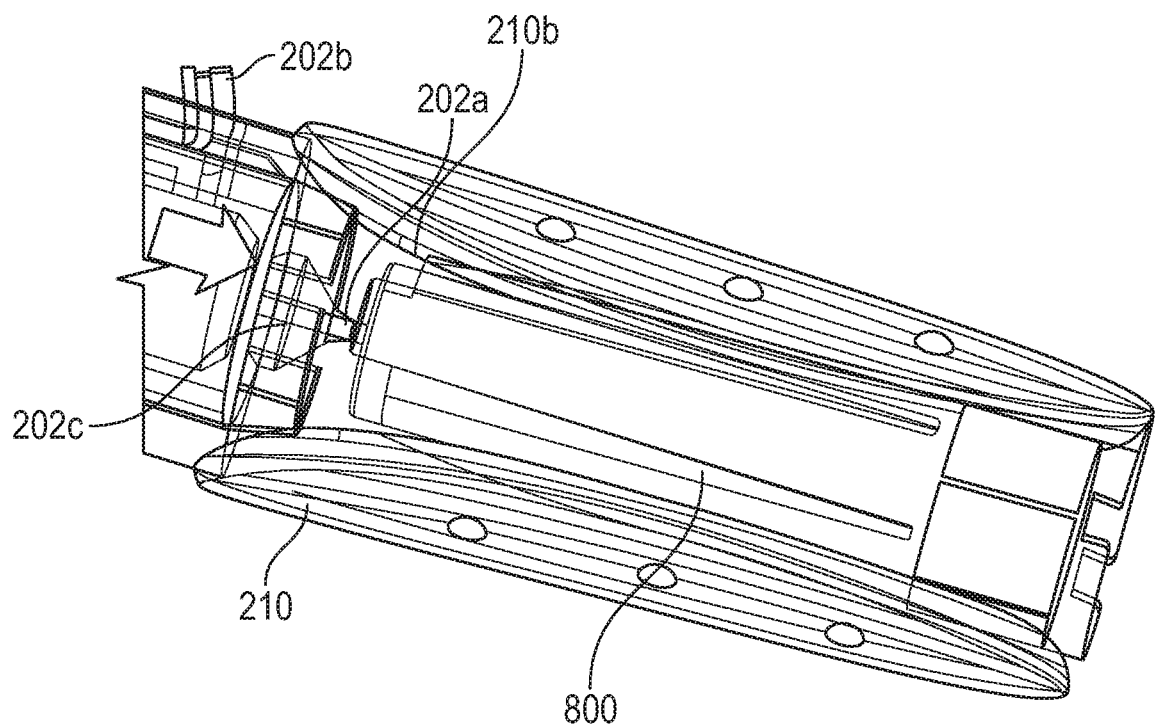
FIG. 8A illustrates another embodiment of a flash chamber that includes a path-defining structure.
Figure 8B:
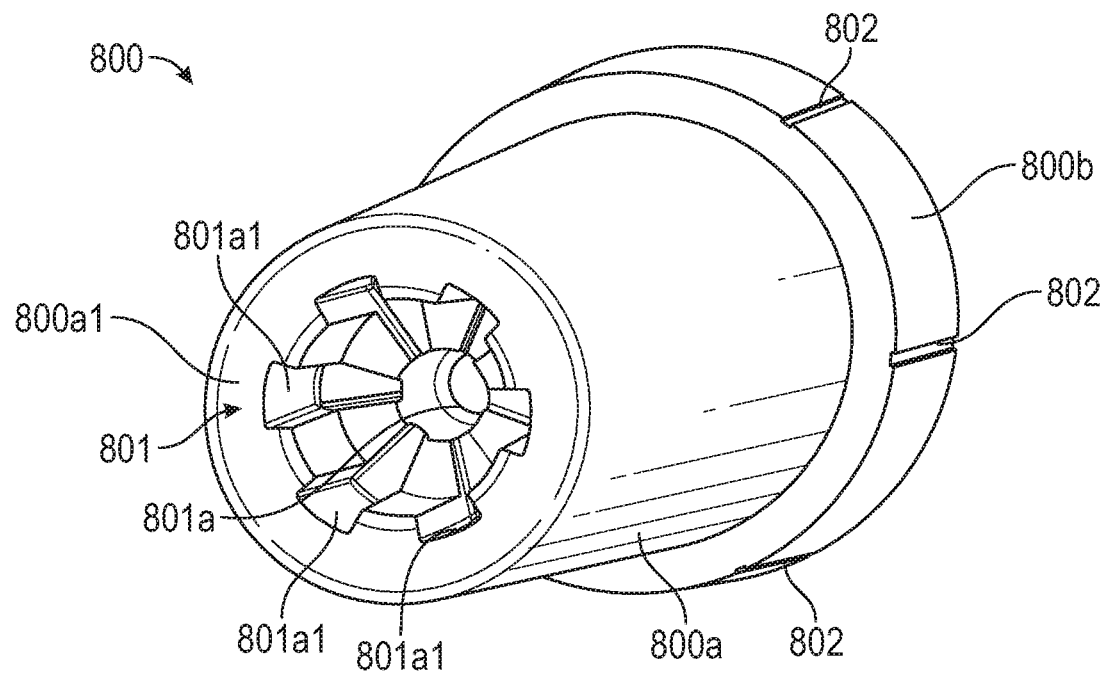
FIG. 8B illustrates the path-defining structure of FIG. 8A in isolation.

FIG. 8A illustrates an embodiment of flash chamber 210 that includes a path-defining structure 800 while FIG. 8B illustrates path-defining structure 800 in isolation. As with path-defining structure 210c, path-defining structure 800 can be positioned within chamber 210b in such a way as to facilitate visualizing the flow of blood into chamber 210b.

Path-defining structure 800 includes a distal portion 800a and a proximal portion 800b. In some embodiments, proximal portion 800b can have an outer dimension that substantially matches an inner dimension of a proximal end of chamber 210b such that a fluid-tight seal is formed between the two components. Proximal portion 800b can include venting grooves 802 which are sized to allow air, but not fluid, to escape from chamber 210b. In other words, proximal portion 800b can function as a vent plug.

Distal portion 800a can have a reduced outer dimension compared to the outer dimension of proximal portion 800b. The inner dimension of chamber 210b with respect to the outer dimension of distal portion 800a can also be configured such that a spacing or channel will exist between distal portion 800a and the inner wall of chamber 210b only along the top of flash chamber 210. For example, as is better shown in FIG. 8C, with path-defining structure 800 inserted into chamber 210b, a channel will exist above path-defining structure 800. However, around the remaining portions of path-defining structure 800, the outer surface of distal portion 800a can contact the inner wall of chamber 210b. In this way, blood/fluid will only be allowed to flow along the outer surface of distal portion 800a within the channel. Since this channel is formed along the top of flash chamber 210, which will be oriented towards the clinician during insertion, the clinician will be able to visualize the rate of blood flow.

To allow blood to flow from the proximal end of needle 202a into this channel, an opening 801 can be formed in a distal end 800a1 of distal portion 800a as is best shown in FIG. 8B. Opening 801 can include a central portion 801a that extends further into distal portion 800a then the remainder of opening 801. The proximal end (or at least a proximal opening) of needle 202a can be positioned within this central portion 801a. A number of leaking channels 801a1 can be symmetrically spaced around an inner surface of opening 801 and can extend from distal end 800a1 to central portion 801a. Any of leaking channels 801a1 can serve as a fluid pathway by which blood escaping the proximal end of needle 202a can flow from central portion 801a towards the channel formed above path-defining structure 800.

Figure 8C:
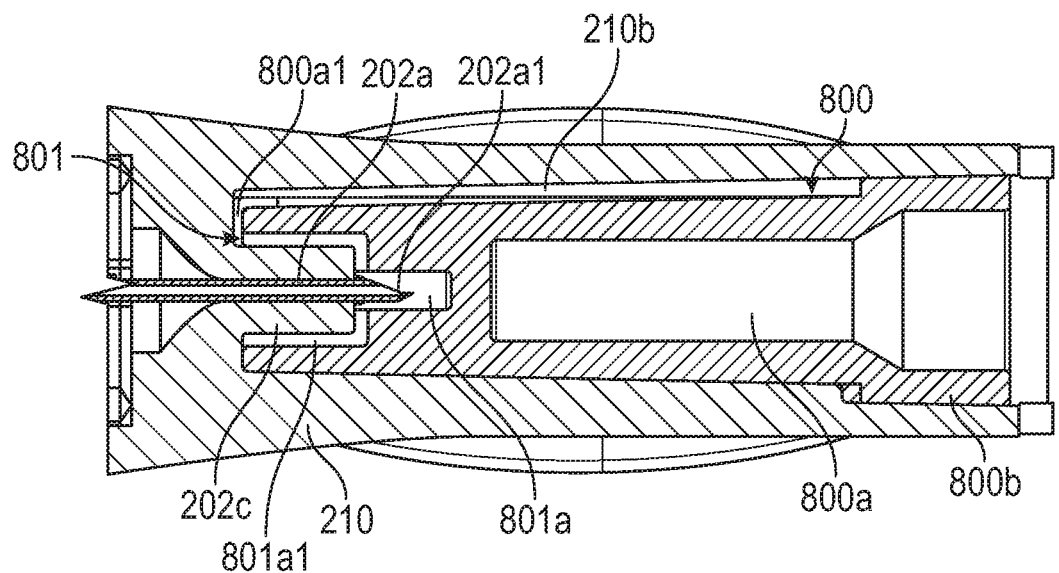
FIG. 8C illustrates a cross-sectional view of the flash chamber of FIG. 8A.
Figure 8D:
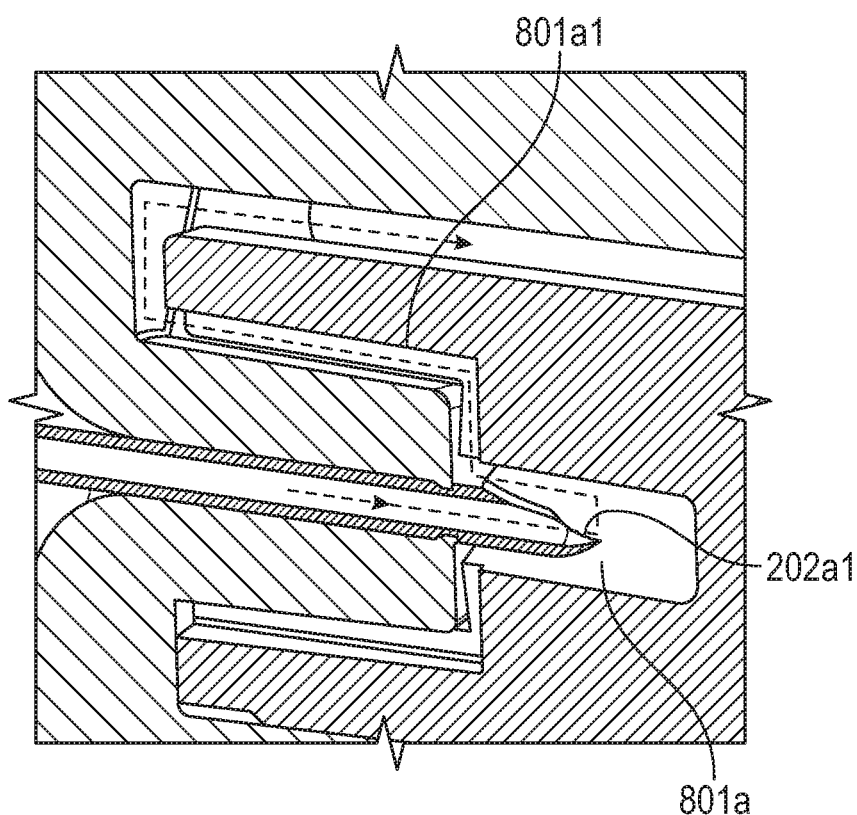
FIG. 8D illustrates another cross-sectional view of the flash chamber of FIG. 8A in which the direction of blood flow is identified.

Leaking channels 801a1 can be symmetrically spaced around opening 801 to thereby allow path-defining structure 800 to be inserted into chamber 210b in any orientation. In other words, regardless of the orientation of path-defining structure 800, at least one leaking channel 801a1 will be positioned in an upward orientation and will intersect with the channel to thereby provide a pathway to the channel. As shown in FIG. 8C, the inner surface of chamber 210b can be shaped such that the channel will wrap around distal end 800a1 at the top of chamber 210b (i.e., a gap will exist between a top portion of distal end 800a1 and the inner surface of chamber 210b). Accordingly, as represented by the arrow in FIG. 8D, blood can flow out of needle 202a via opening 202a1 and into central portion 801a. Then, although the blood may flow into each of leaking channels 801a1, a fluid pathway will only be provided between the leaking channel that is oriented upward due to distal end 800a1 contacting the inner wall of chamber 210b where the other leaking channels are positioned. Therefore, as the blood fills central portion 801a and leaking channels 801a1, it will ultimately flow around the top portion of distal end 800a1 and then proximally within the channel.

Figure 8E:
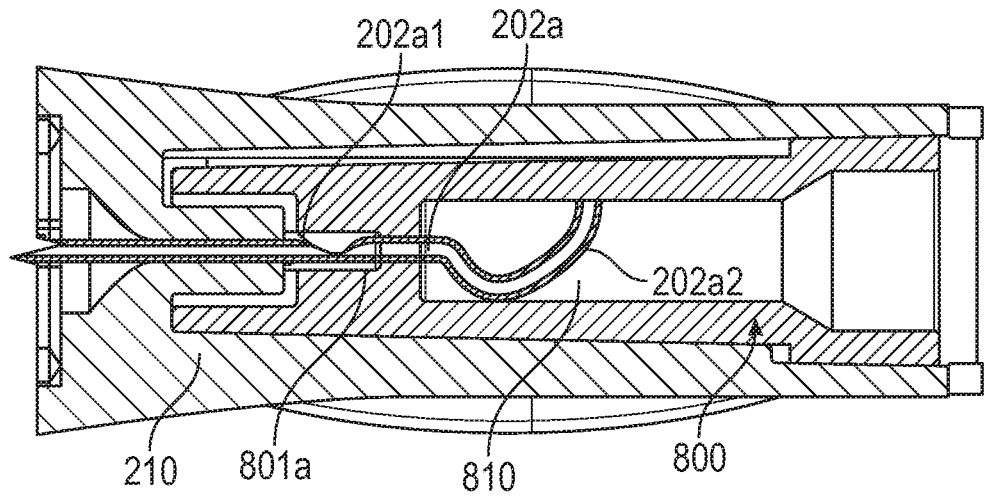
FIG. 8E illustrates an embodiment of the flash chamber of FIG. 8A in which a proximal end of the needle extends into and is secured within the path-defining structure.

To secure needle 202a and to ensure that opening 202a1 remains positioned within central portion 801a, various techniques can be employed. For example, in FIG. 8E, needle 202a is shown as having a proximal portion 202a2 that extends proximally beyond opening 202a1 and through a proximal wall of central portion 801a. In this embodiment, path-defining structure 800 includes a proximal chamber 810 opposite central portion 801a within which proximal portion 202a2 of needle 202a is positioned. Proximal portion 202a2 can be curled or otherwise altered to prevent it from being pulled distally through the passageway between central portion 801a and proximal chamber 810. Also, in some embodiments, adhesive potting may be deposited within proximal chamber 810 around proximal portion 202a2 to further secure proximal portion 202a2. In such embodiments, the adhesive potting may additionally seal the passageway to prevent blood from flowing into proximal chamber 810. Alternatively, the passageway may be sized such that proximal portion 202a2 alone blocks fluid flow into proximal chamber 810.

Figure 8F:
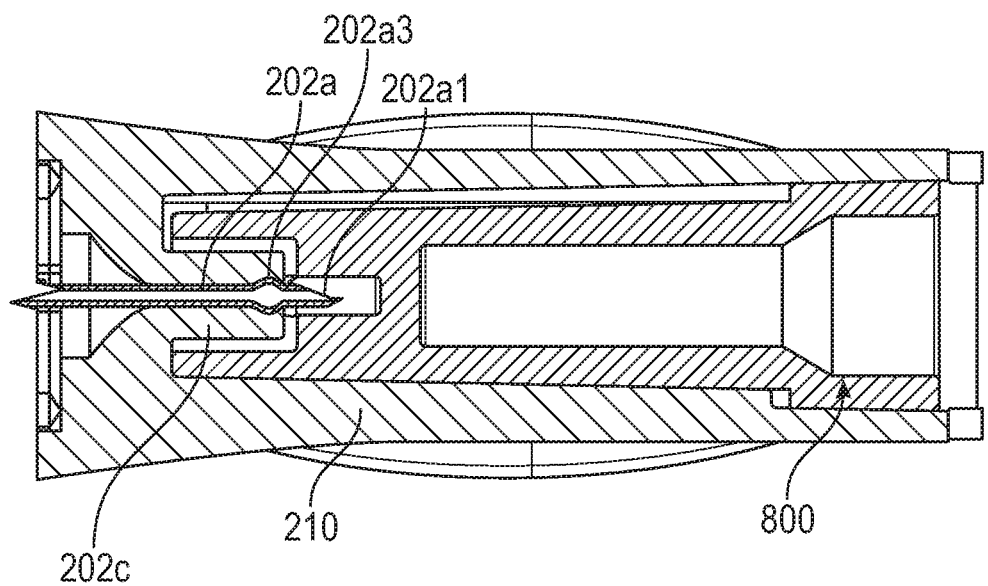
FIG. 8F illustrates an embodiment of the flash chamber of FIG. 8A in which the needle includes a bulge for securing the needle to the flash chamber.

FIG. 8F illustrates an alternate embodiment for securing needle 202a in position. As shown, needle 202a may include a bumped area 202a3 (which may integrally molded, separately formed and coupled to needle 202a with an adhesive, or otherwise formed) that has an outer dimension sufficient to prevent needle 202a from being pulled through needle retaining portion 202c. Bumped area 202a3 can be positioned relative to opening 202a1 so that opening 202a1 remains positioned within central portion 801a. In some embodiments, needle retaining portion 202c may include a recessed section into which bumped area 202a3 can be positioned to further prevent area 202a from moving in a proximal or distal direction.

Figure 8G:
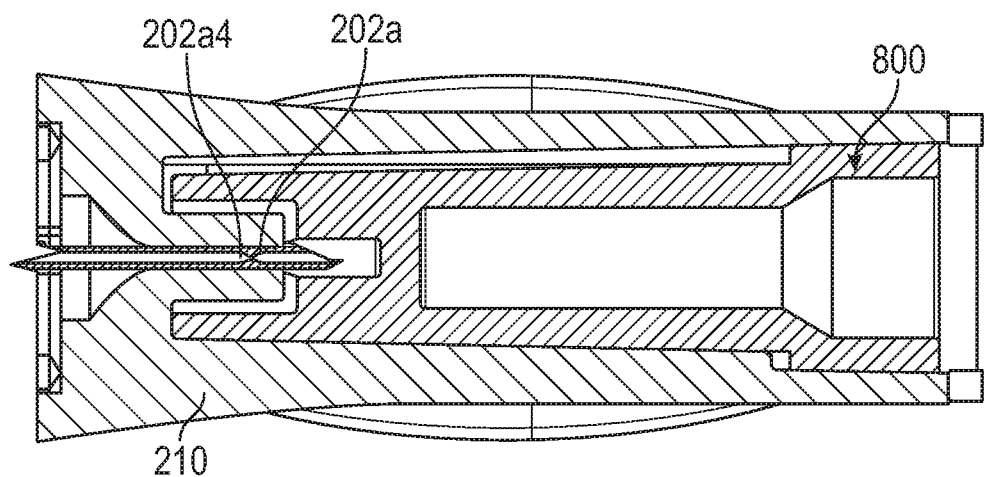
FIG. 8G illustrates an embodiment of the flash chamber of FIG. 8G in which the needle includes a crimp to slow the rate of blood flow into the flash chamber.

In some embodiments, needle 202a may be modified to reduce the rate at which blood will flow through the needle. For example, in FIG. 8G, needle 202a is shown as having a crimp 202a4 towards its proximal end. Crimp 202a4 reduces the inside dimension of needle 202a thereby slowing the rate at which blood will flow into central portion 801a. Reducing the rate of blood flow into central portion 801a will likewise reduce the rate of blood flow along the channel formed above path-defining structure 800 thereby facilitating identifying when needle 202a has been properly positioned within the patient.

Figure 9A:
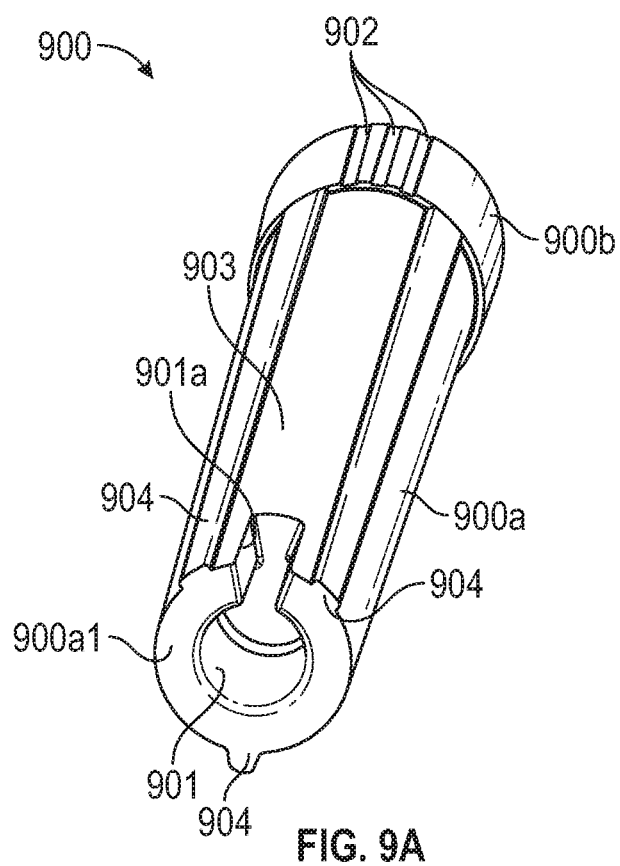
FIGS. 9A and 9B illustrate different views of an alternate embodiment of a path-defining structure that can be employed within a flash chamber.
Figure 9B:
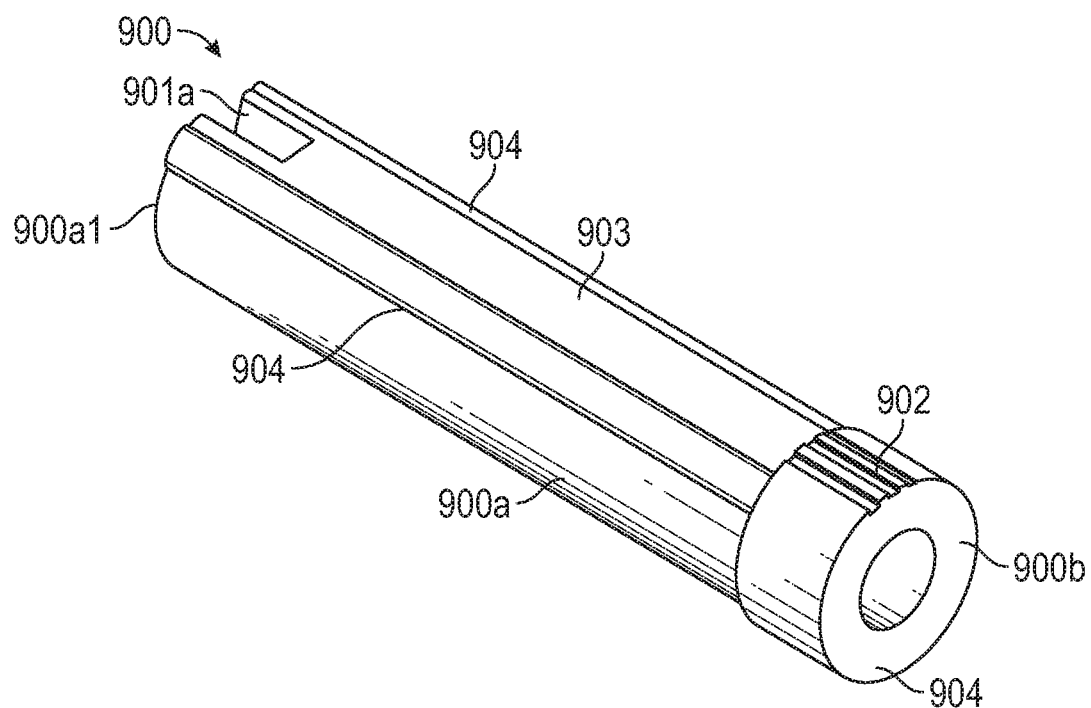

FIGS. 9A and 9B illustrate another embodiment of a path-defining structure 900 that can function in a similar manner as path-defining structure 800. In particular, path-defining structure 900 can be configured to cause blood to flow along a visualization channel formed at the top of flash chamber 210.

Path-defining structure 900 can include a distal portion 900a and a proximal portion 900b. Proximal portion 900b can include venting grooves 902 that function to vent air from a proximal end of flash chamber 210. Unlike distal portion 800a of path-defining structure 800 which can be inserted into chamber 210b in any orientation, distal portion 900a can include a visualization channel 903 and various alignment ribs 904 that are configured for a particular orientation. The inner surface of chamber 210b can be configured to accommodate alignment ribs 904 in such a manner that path-defining structure 900 will be oriented with visualization channel 903 facing upwards. For example, chamber 210b could include lengthwise grooves or tabs which interface with alignment ribs 904 to require insertion of path-defining structure 900 in the correct orientation and to prevent rotation. Alternatively, chamber 210*b* could be configured to form a frictional fit with path-defining structure 900 which would prevent its rotation once inserted into the chamber. In such cases, alignment ribs 904 would not be required.

Figure 9C:
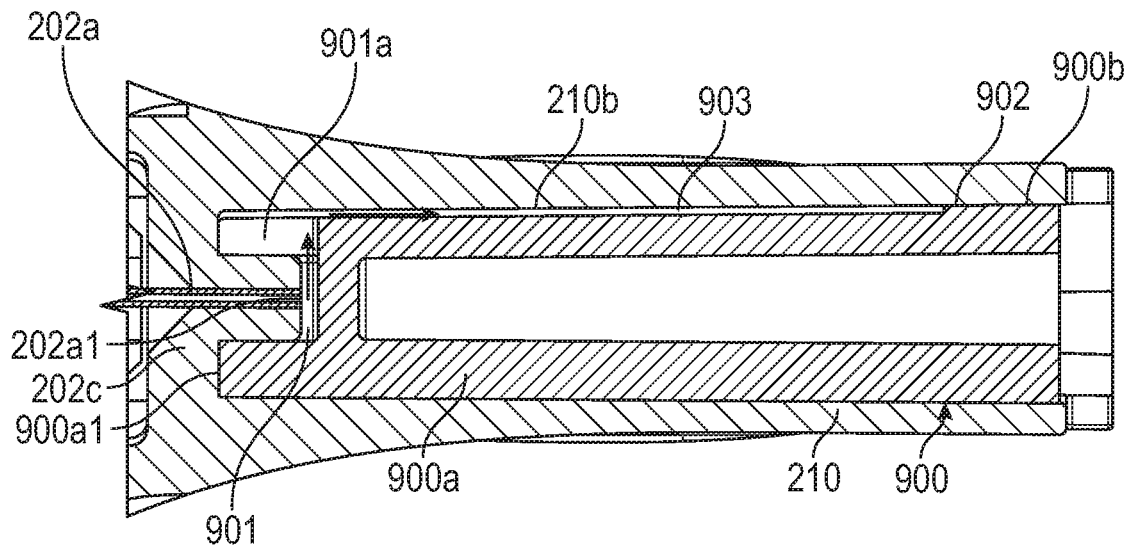
FIG. 9C illustrates a cross-sectional view of a flash chamber that includes the path-defining structure of FIGS. 9A and 9B.

Distal portion 900*a* of path-defining structure 900 can include a distal end 900*a*1 having an opening 901. A leaking channel 901*a* can extend between opening 901 and visualization channel 903. In a similar manner as described above, blood can flow out of opening 202*a*1 into opening 901 through leaking channel 901*a* and into visualization channel 903 as represented by the arrows in FIG. 9C. Although not depicted in this embodiment, the various configurations of needle 202*a* shown in FIGS. 8E-8G can also be employed in conjunction with path-defining structure 900.

Figure 10:
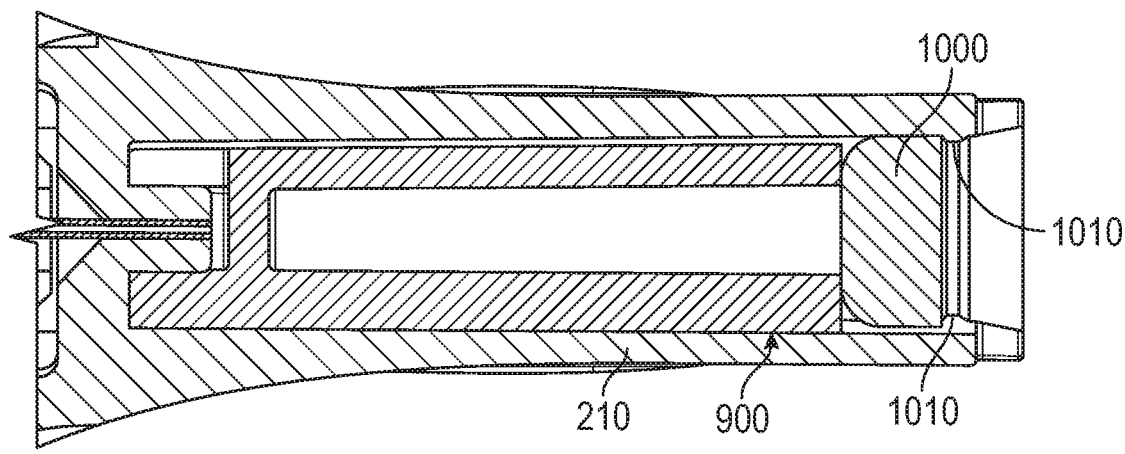
FIG. 10 illustrates an embodiment of a flash chamber that includes a path-defining structure and a vent plug that secures the path-defining structure within the flash chamber.

FIG. 10 illustrates an embodiment of a flash chamber 210 in which a vent plug 1000 is employed in place of distal portion 900*b*. Also, although not shown, vent plug 1000 could equally be employed in place of distal portion 800*b*. As depicted in FIG. 10, vent plug 1000 is separate from and positioned proximally to path-defining structure 900. Vent plug 1000 can primarily function to vent air but block fluid. However, in some embodiments, vent plug 1000 may also be configured to secure path-defining structure 800/900 in place. For example, flash chamber 210 can include protrusion(s) 1010 that are positioned proximally to vent plug 1000 when vent plug 1000 is inserted into chamber 210*b*. Protrusions 1010 can prevent vent plug 1000, and therefore path-defining structure 800/900, from moving proximally within chamber 210*b*. In some embodiments, a single protrusion 1010 may extend fully around the entire inner circumference of flash chamber 210, while in other embodiments, multiple protrusions 1010 may be spaced around the inner circumference. Also, in some embodiments, protrusion 1010 may extend fully around the inner circumference (thereby forming an inner ring) and can be positioned such that it extends into vent plug 1000 (e.g., shifted to the left form what is shown in FIG. 10). In these embodiments, protrusion 1010 can not only function to retain vent plug 1000 within chamber 210*b* but can also form a seal around vent plug 1000.

Figure 11A:
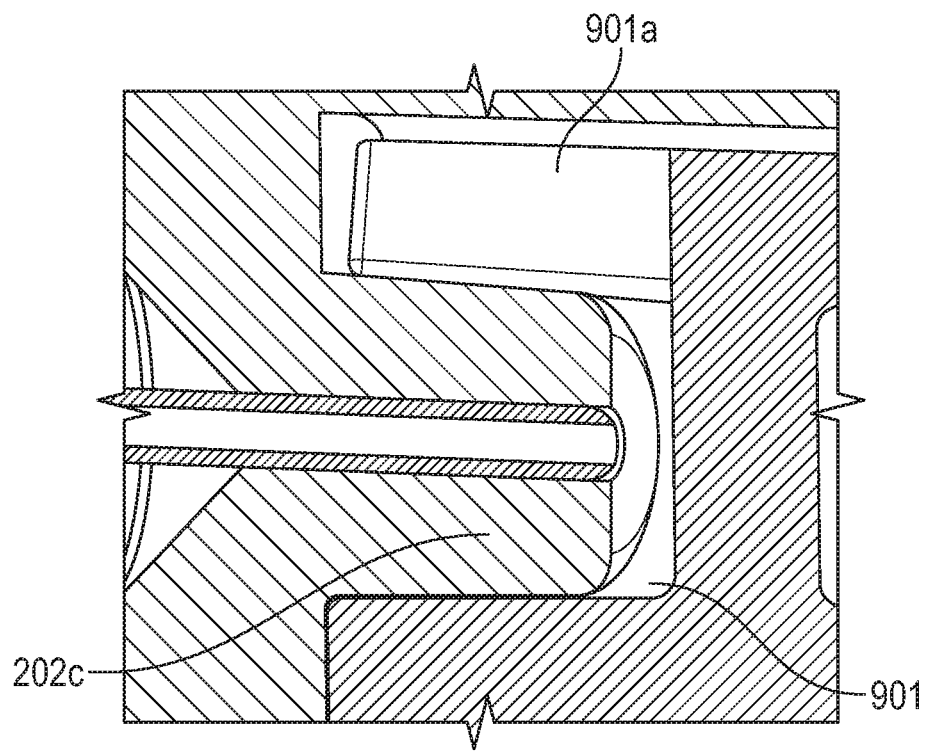
FIGS. 11A-11C each illustrate an example of how a path-defining structure can be secured within a flash chamber.
Figure 11B:
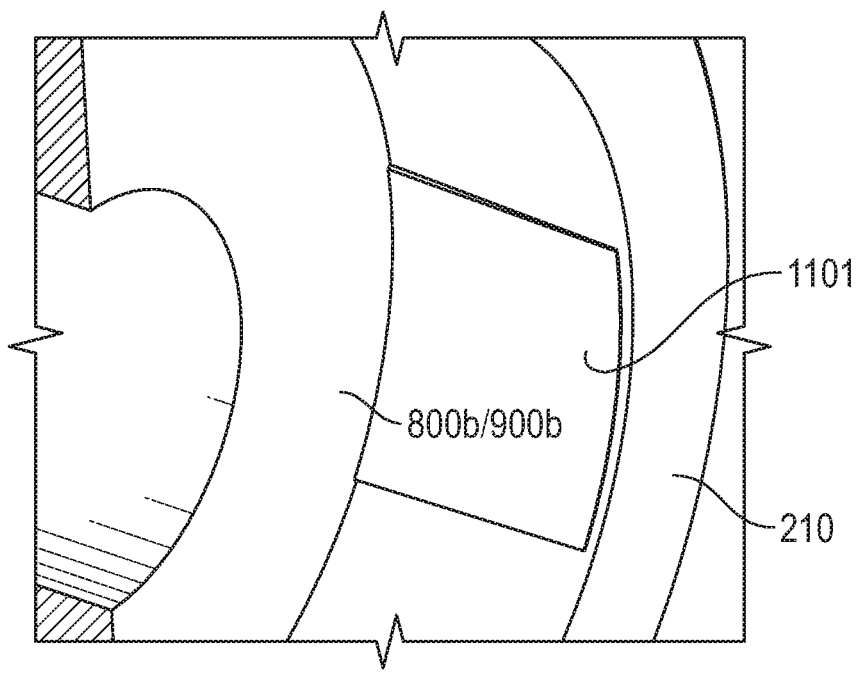
Figure 11C:
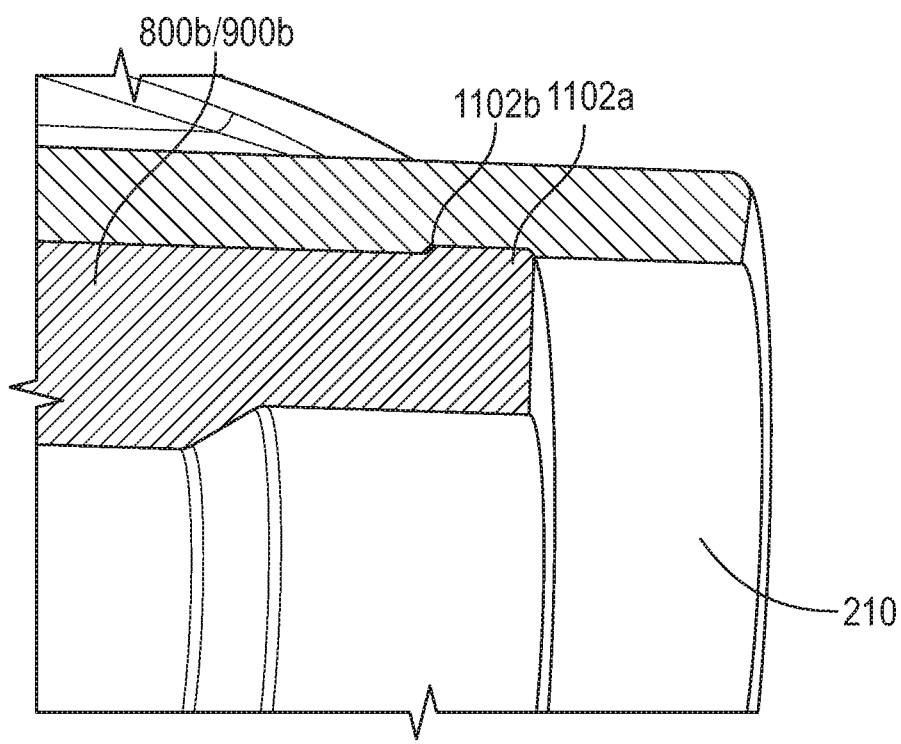

FIGS. 11A-11C each represent a different way in which path-defining structure 800 or 900 could be secured within chamber 210*b*. In FIG. 11A, opening 901 is shown as having an inner dimension that corresponds closely with the outer dimension of needle retaining portion 202*c* such that a press-fit interface is formed. Opening 801 could equally be configured in this manner. Alternatively, opening 801/901 could be molded overtop needle retaining portion 202*c*.

In FIGS. 11B and 11C, path-defining structure 800/900 can be retained within chamber 210*b* using an interface between proximal portion 800*b*/900*b* and an inner surface of chamber 210*b*. In FIG. 11B, chamber 210*b* can include a sloped retention bump 1101. The slope of bump 1101 can cause a distal facing ledge to be formed against which a proximal end of proximal portion 800*b* or 900*b* contacts. This sloping facilitates inserting path-defining structure 800 or 900 but prevents it from being later withdrawn.

FIG. 11C illustrates an example where proximal portion 800*b* or 900*b* includes a retention rib 1102*a* which inserts into a retention trench 1102*b* formed on an inner surface of chamber 210*b*. During assembly, path-defining structure 800 or 900 can be inserted into chamber 210*b* until retention rib 1102*a* inserts into retention trench 1102*b*. At this point, retention rib 1102*a* will prevent the path-defining structure from being proximally withdrawn.

Figure 12A:
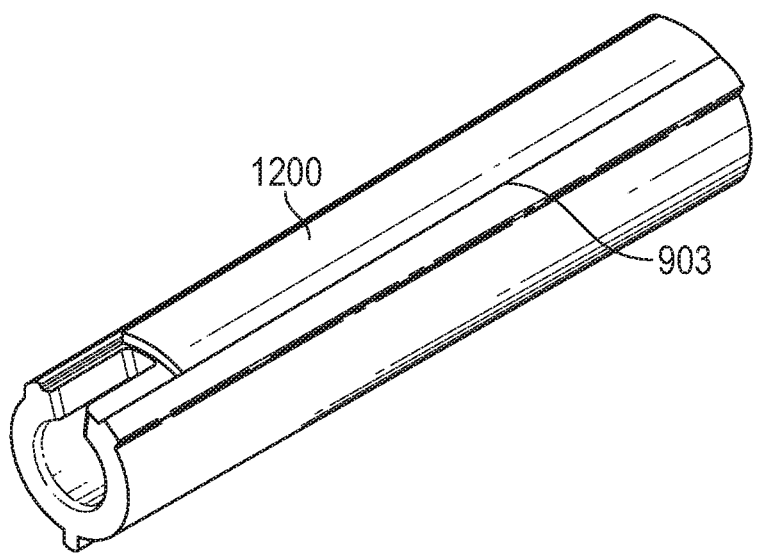
FIGS. 12A and 12B each illustrate an example of how a porous material can be included within a portion of a visualization channel of a path-defining structure.
Figure 12B:
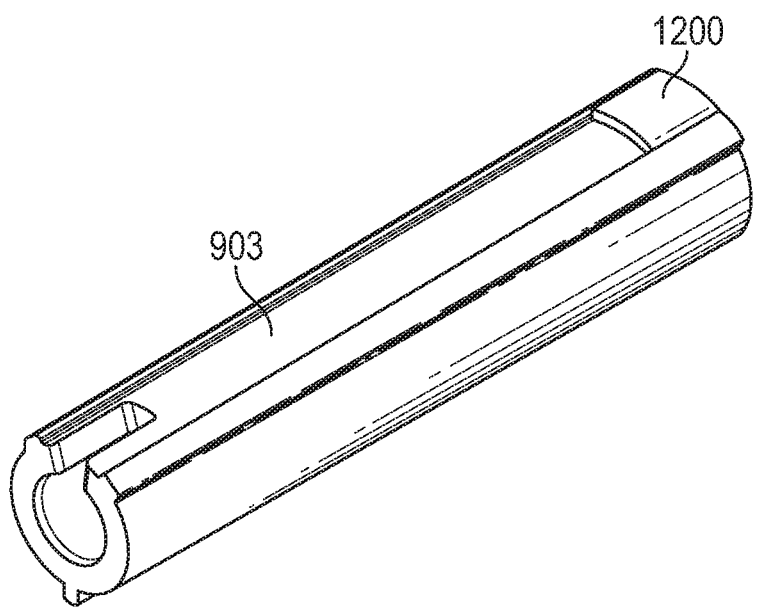

In some embodiments, a porous material could be employed within the channel created by the path-defining structure. For example, in FIG. 12A, a porous material 1200 can be fabricated into visualization channel 903 and extend through the portion of proximal portion 900*b* that includes venting grooves 902. Porous material 1200 can function to vent air while also wicking the blood at a rate that will be easily visualized. Alternatively, porous material 1200 may only be positioned within the portion of proximal portion 900*b* as shown in FIG. 12B.

Figure 13:
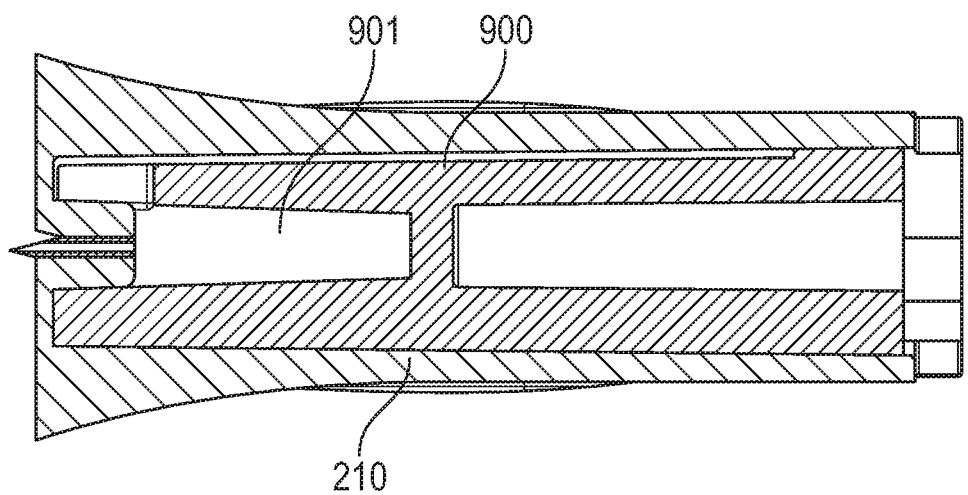
FIG. 13 illustrates how the volume of an opening in the path-defining structure can be increased to accommodate different insertion techniques.
Figure 14:
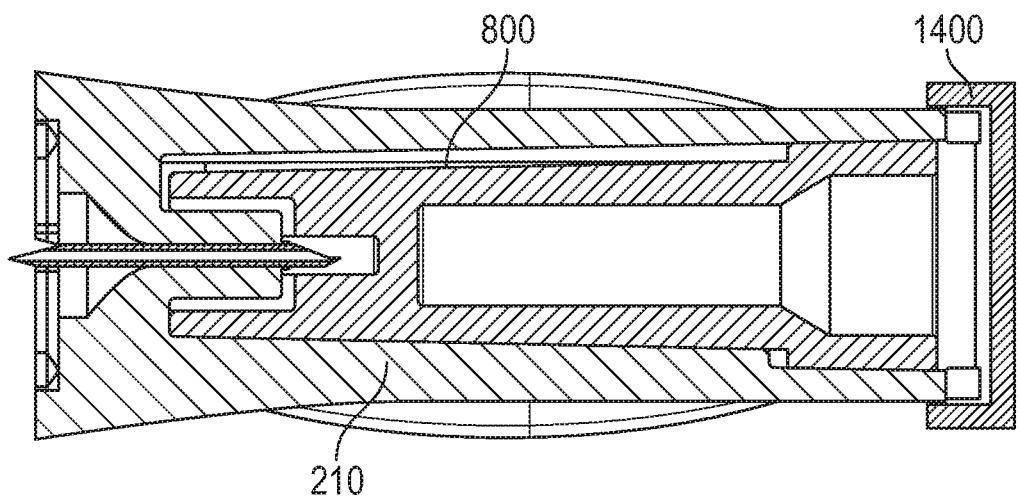
FIG. 14 illustrates how a flash chamber can include a sealing cap to accommodate different insertion techniques.

FIGS. 13 and 14 each depict additional variations that can be made to embodiments that employ either path-defining structure 800 or 900. In FIG. 13, opening 901 is shown having a larger depth. With this larger depth, more fluid volume will be required before blood will flow through the channel. Accordingly, the depth of opening 801 or 901 can be selected to generally control when visual feedback of proper vein confirmation will be provided. In FIG. 14, a sealing cap 1400 is positioned overtop the proximal opening of flash chamber 210. Sealing cap 1400 can block the flow of air until removed. Therefore, sealing cap 1400 can be employed in situations where extension tube 103 is pre-primed with saline to prevent the saline from flowing proximally into flash chamber 210. More specifically, with sealing cap 1400 in place, the saline will only be allowed to flow distally within needle 202*a*. After insertion of the needle, sealing cap 1400 can be removed to allow flash chamber 210 to be employed in the manner described above.

Various embodiments of the present invention further comprise a safety mechanism configured to secure the sharpened, distal tip of the introducer needle following removal and separation of the needle hub from the catheter adapter. A safety mechanism may include any compatible device known in the art. In some instances, the safety mechanism is configured to interact with a needle feature, such as a ferrule, notch, crimp or bump on the cannula. The crimp or bump formed in the cannula causes a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the catheter adapter prior to catheterization. For some configurations, the assembled position of the safety mechanism is between the proximal end of the needle hub and the proximal end of the catheter adapter or stabilization platform, wherein the safety mechanism does not overlap the catheter adapter or stabilization platform. In some instances, a portion of the safety mechanism is positioned within the catheter adapter, with the balance of the safety mechanism being positioned external to the catheter adapter, such as within the needle hub. In some embodiments, a portion of the catheter adapter or stabilization platform is extended proximally to provide a housing in which at least a portion of the safety mechanism is housed. In some instances, the entire safety mechanism is housed within the housing of the catheter adapter or stabilization platform prior to catheterization.

In some embodiments, the assembled position of the safety mechanism positions the proximal end of the catheter adapter between the distal end of the safety mechanism and a distal end of a paddle grip of the needle hub. In some instances, the assembled position of the safety mechanism positions the proximal end of the catheter adapter between the distal end of the safety mechanism and a proximal end of a paddle grip of the needle hub. In some instances, a portion of the safety mechanism overlaps a portion of a paddle grip of the needle hub. In some embodiments, at least some portion of at least one of the catheter adapter and the paddle grip overlaps at least some portion of the safety mechanism. In some embodiments, no portion of the catheter adapter or paddle grip overlaps any portion of the safety mechanism.

In some embodiments, a defeatable mechanical connection is provided between the safety mechanism and at least one other component of the access device. In some embodiments, a distal end of the safety mechanism is selectively coupled to a proximal end of the catheter adapter. In one embodiment, the safety mechanism interlocks internally to the proximal end of the catheter adapter. In one embodiment, the safety mechanism interlocks externally to the proximal end of the catheter adapter. In some embodiments, a distal end of the safety mechanism is selectively coupled to a proximal end of the stabilization platform. In some embodiments, a surface of the safety mechanism is selectively coupled to at least one surface of at least one of the catheter adapter, a blood control valve, an extension tube, and the stabilization platform. In some instances, the mechanical connection is defeated upon securement of the needle tip within the safety mechanism.

In some embodiments, a particular catheter device, such as, for example, the catheter device of any of the FIGS. 1-14, may include a needle safety mechanism. The safety mechanism may include any safety mechanism configured to secure a sharpened, distal tip of an introducer needle when the needle is withdrawn from a catheter of the particular catheter device, preventing accidental needle sticks.

The safety mechanism may be coupled with the particular catheter device in any number of ways. In some embodiments, the safety mechanism may include an internal interlock in which the safety mechanism is coupled with an internal surface of a catheter adapter. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter. In some embodiments, the safety mechanism may be coupled with an external surface of the catheter adapter and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter adapter, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a paddle grip. In some embodiments, in the assembled position prior to catheterization, the proximal end of the catheter adapter body may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter adapter and the grip overlaps at least some portion of the safety mechanism. In some embodiments, no portion of the catheter adapter body or the grip overlaps any portion of the safety mechanism.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An IV access device comprising:
   a catheter adapter from which a catheter extends distally;
   an extension tube coupled to the catheter adapter; and
   a needle hub from which a needle extends distally, the needle hub being coupled to the catheter adapter such that the needle extends through the catheter;
   wherein the needle hub further includes a flash chamber that is in fluid communication with a lumen of the needle thereby allowing blood to flow into the flash chamber when a distal tip of the needle is contained within a patient's vein, wherein a proximal end of the flash chamber includes a vent plug, wherein the flash chamber includes:
      a path-defining structure forming a path for blood to flow within the chamber, wherein the path includes a spiral path formed around an outer surface of the path-defining structure and having a distal end and a proximal end, wherein the distal end of the spiral path is proximal to the needle, wherein the proximal end of the spiral path is proximate the vent plug; or
      a path that commences from an opening in a distal end of the path-defining structure and passes through a leaking channel to a visualization channel formed along an outer surface of the path-defining structure.

2. The IV access device of claim 1, wherein a proximal end of the needle includes an opening that is positioned within a chamber of the flash chamber.

3. The IV access device of claim 2, wherein the flash chamber includes a plug positioned proximal to the chamber, the plug venting air but blocking the flow of blood to an external environment.

4. The IV access device of claim 2, wherein the needle hub includes a needle retaining portion through which the needle extends, the opening of the needle being positioned proximal to the needle retaining portion.

5. The IV access device of claim 1, wherein the opening of the needle extends into the path formed by the path-defining structure.

6. The IV access device of claim 1, wherein the needle includes a notch positioned towards the distal tip of the needle, wherein blood flowing through the notch and into the catheter provides a first confirmation of proper catheter placement and blood flowing into the flash chamber provides second confirmation of proper catheter placement.

7. The IV access device of claim 1, wherein the flash chamber is removable from the needle hub.

8. The IV access device of claim 7, wherein the flash chamber is compressible to allow blood contained within the chamber to be ejected from the chamber.

9. The IV access device of claim 7, wherein the needle hub includes a female luer port, the flash chamber being configured to be coupled to the female luer port.

10. The IV access device of claim 1, wherein the catheter adapter includes a wing and the needle hub includes a paddle grip.

11. An IV access device comprising:
    a catheter adapter from which a catheter extends distally;
    an extension tube coupled to the catheter adapter;
    a needle hub from which a needle extends distally, the needle hub being coupled to the catheter adapter such that the needle extends through the catheter, the needle hub including a flash chamber, a proximal end of the needle forming a fluid pathway for blood to flow into the flash chamber, the flash chamber including a plug that vents air but blocks the flow of blood thereby allowing blood to flow into the flash chamber when a distal tip of the needle is contained within a patient's vein, wherein the flash chamber includes a path-defining structure forming a path for blood to flow within the chamber, wherein a proximal end of the flash chamber includes a vent plug, wherein the path-defining structure includes a spiral path formed around an outer surface of the path-defining structure and having a distal end and a proximal end, wherein the distal end of the spiral path is proximal the needle, wherein the proximal end of the spiral path is the vent plug.

12. The IV access device of claim 11, wherein the flash chamber is removable from the needle hub.

13. The IV access device of claim 11, wherein the plug is formed by a portion of the path-defining structure.

14. The IV access device of claim 11, wherein the flash chamber couples to the needle hub via a female luer port.

15. The IV access device of claim 11, wherein the catheter adapter includes a wing and the needle hub includes a paddle grip.

* * * * *